United States Patent
McCarron et al.

(10) Patent No.: US 12,100,920 B2
(45) Date of Patent: Sep. 24, 2024

(54) COAXIAL CONNECTOR

(71) Applicant: Zomedica Biotechnologies LLC, Ann Arbor, MI (US)

(72) Inventors: Kevin Thomas McCarron, Bend, OR (US); Rick Morton, Bend, OR (US); Christopher Jennings Madsen, Waseca, MN (US)

(73) Assignee: Zomedica Biotechnologies LLC, Ann Arbor, MI (US)

( * ) Notice: Subject to any disclaimer, the term of this patent is extended or adjusted under 35 U.S.C. 154(b) by 282 days.

(21) Appl. No.: 17/787,176

(22) PCT Filed: Dec. 18, 2020

(86) PCT No.: PCT/US2020/066115
§ 371 (c)(1),
(2) Date: Jun. 17, 2022

(87) PCT Pub. No.: WO2021/127501
PCT Pub. Date: Jun. 24, 2021

(65) Prior Publication Data
US 2023/0020293 A1 Jan. 19, 2023

Related U.S. Application Data

(60) Provisional application No. 62/950,661, filed on Dec. 19, 2019.

(51) Int. Cl.
*H01R 24/50* (2011.01)
*G01N 29/02* (2006.01)
(Continued)

(52) U.S. Cl.
CPC .......... *H01R 24/50* (2013.01); *G01N 29/022* (2013.01); *G01N 29/32* (2013.01);
(Continued)

(58) Field of Classification Search
CPC .......... H01R 24/00–52; H01R 2103/00; H01R 2201/20; G01N 29/00–036; G01N 29/022; G01N 2291/022; G01N 2291/0426
See application file for complete search history.

(56) References Cited

U.S. PATENT DOCUMENTS 5,046,966 A * 9/1991 Snyder ............... H01R 13/6592
439/98
5,795,162 A 8/1998 Lambert
(Continued)

OTHER PUBLICATIONS

International Search Report and Written Opinion mailed Mar. 23, 2021 in International Application No. PCT/US2020/066115, 9 pages.
Mielke et al., "High-Speed Fixture Interconnects for Mixed-Use Signal IC Testing," International Test Conference, 1990, pp. 891-895.
(Continued)

*Primary Examiner* — Nguyen Q. Ha
(74) *Attorney, Agent, or Firm* — Standley Law Group LLP; Jeffrey S. Standley; Bryan P. Finneran

(57) ABSTRACT

A connector assembly and method of attaching the same to one or more biosensor module boards. The connector assembly includes a body portion defining a first surface and a second surface opposite the first surface. The connector assembly also includes a coaxial RF connector positioned in the body portion and extending between the first surface and the second surface. The coaxial RF connector includes a ground ring, an RF pin positioned within the ground ring, and dielectric therebetween. The connector assembly is configured to be coupled to an RF detection board such that the coaxial RF connector is operably coupled thereto. The connector assembly is also configured to be connected to a biosensor module board such that the coaxial RF connector is operably connected thereto.

20 Claims, 11 Drawing Sheets

(51) Int. Cl.
*G01N 29/32* (2006.01)
*H01R 103/00* (2006.01)

(52) U.S. Cl.
CPC ............... *G01N 2291/022* (2013.01); *G01N 2291/0426* (2013.01); *H01R 2103/00* (2013.01); *H01R 2201/20* (2013.01)

(56) References Cited

U.S. PATENT DOCUMENTS

| | | |
|---|---|---|
| 7,936,106 B2 | 5/2011 | Lee et al. |
| 2006/0141811 A1 | 6/2006 | Shichida et al. |
| 2011/0237125 A1 | 9/2011 | Montena |
| 2014/0154697 A1 | 6/2014 | Johal et al. |
| 2015/0060306 A1 | 3/2015 | Ueno et al. |
| 2018/0064364 A1 | 3/2018 | Oziel et al. |
| 2018/0231475 A1 | 8/2018 | Brown et al. |
| 2020/0036143 A1* | 1/2020 | Lyu ............... H01R 24/545 |

OTHER PUBLICATIONS

Kayano et al., "EMI Resulting from Interconnected Printed Circuit Boards by a Coaxial Cable," 2007 IEEE International Symposium on Electromagnetic Compatibility, 5 pages.

Rosas et al., "Development of a 1.85 mm Coaxial Blind Mating Interconnect for ATE Applications," 2017 IEEE MTT-S International Microwave Symposium (IMS), pp. 503-506.

Sasaki et al., "Coaxial SMT Module Connector for High-speed MCM," Proceedings of IEEE 43rd Electronic Components and Technology Conference (ECTC'93), pp. 446-451.

Dong et al., "A Novel Approach for Broadband High Frequency Interconnect Between Substrates," 2018 International Conference on Microwave and Milimeter Wave Technology (ICMMT), 3 pages.

International Preliminary Report on Patentability mailed May 17, 2022 in International Application No. PCT/US2020/066115, 7 pages.

Extended European Search Report from Application No. EP 20901890.2, mailed Jul. 27, 2023, 8 pages.

* cited by examiner

COAXIAL CONNECTOR

CROSS-REFERENCE TO RELATED APPLICATION

The present application is a U.S. National Stage patent application of International Patent Application No. PCT/US2020/066115, filed on Dec. 18, 2020, which claims the benefit of U.S. Provisional Application No. 62/950,661 filed Dec. 19, 2019, the benefit of which is claimed and the disclosures of which are incorporated herein by reference in their entirety.

TECHNICAL FIELD

This disclosure generally relates to a repeatable high performance radio frequency (RF) connection for biosensor devices, such as bulk acoustic wave (BAW) sensor devices.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, vims, bacteria, etc.), and the product of this highly specific reaction is converted into a measurable quantity by a transducer. Other sensors may utilize a nonspecific binding material capable of binding multiple types or classes of molecules or other moieties that may be present in a sample. The term "functionalization material" may be used herein to generally relate to both specific and nonspecific binding materials. Transduction methods used with biosensors may be based on various principles, such as electrochemical, optical, electrical, acoustic, etc. Among these, acoustic transduction offers a number of potential advantages, such as being real time, label-free, and low cost, as well as exhibiting high sensitivity.

An acoustic wave device employs an acoustic wave that propagates through or on the surface of a specific binding material, whereby any changes to the characteristics of the propagation path affect the velocity and/or amplitude of the wave. Acoustic wave devices are commonly fabricated by micro-electro-mechanical systems (MEMS) fabrication techniques, owing to the need to provide microscale features suitable for facilitating high-frequency operation. Presence of functionalization material on or over an active region of an acoustic wave device permits an analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, amplitude-magnitude, and/or phase characteristics of the acoustic wave device and can be correlated to a physical quantity being measured.

Existing BAW devices may be coupled on a biosensor module board that is connected to an instrument that will interrogate the biosensor. The biosensor module board may be connected to the interrogating instrument (e.g., an RF detection board) through a typical connector (e.g., coupled to the instrument and configured to be connected to the biosensor module board). However, one issue with existing connectors is that the connector may include poor RF performance of the electrical interface between the biosensor module and the interrogating instrument. For example, a radiative ground return path may not allow repeatable and reliable electrical connection. Therefore, it may be desirable to use a connector that provides repeatable and reliable high-performance RF connection for biosensor devices.

SUMMARY

Embodiments described herein may provide a coaxial connector for making reliable, repeatable blind electrical connections between a biosensor module board and an instrument that will interrogate the biosensor with minimal mechanical wear. The connector may include combining an S-band coaxial element with digital control lines and a low frequency meter sense line to allow a stable, reliable connection of an RF module board that contains a BAW biosensor, microfluidics and a conductivity meter to an RF detection board inside an interrogation instrument.

Prior to the implementation of the embodiments described herein, previous systems encountered issues when operating at a higher frequency (e.g., above 2175 MHz) that were insignificant at lower frequencies. Therefore, the RF performance of those previous systems were quite poor at higher frequencies. As described herein, the present connector assembly includes a coaxial arrangement of the RF pin to provide RF ground terminals proximate the RF pin. As such, the RF power flow may flow from the RF pin to the BAW die with the reflected power following the same path back to the RF ground terminals. Furthermore, this arrangement may greatly reduce the radiation of RF power to other sides of the biosensor module board.

Those skilled in the art will appreciate the scope of the present disclosure and realize additional aspects thereof after reading the following detailed description in association with the accompanying drawings.

An illustrative system may include an RF detection board, a biosensor module board, and a connector assembly. The biosensor module board may include an electronic board and a fluidic sensor device. The connector assembly may be operably coupled to the RF detection board and configured to be operably connected to the biosensor module board. The connector assembly may include a coaxial RF connector. The coaxial RF connector may include a ground ring, an RF pin positioned within the ground ring, and dielectric therebetween.

In one or more embodiments, the coaxial RF connector is configured to conduct frequencies greater than or equal to 2 GHz and dissipate into the ground ring.

In one or more embodiments, the coaxial RF connector is configured to conduct frequencies greater than or equal to 2.5 GHz and dissipate into the ground ring.

In one or more embodiments, the dielectric comprises Teflon.

In one or more embodiments, an RF signal is configured to be transmitted from the RF pin to the fluidic sensor device and then to the ground ring.

In one or more embodiments, the ground ring directly contacts the electronic board of the biosensor module board.

In one or more embodiments, the coaxial RF connector extends through the connector assembly between a first surface and a second surface, wherein the coaxial RF connector is operably connected to the biosensor module board proximate the first surface of the connector assembly and the coaxial RF connector is operably coupled to the RF detection board proximate the second surface of the connector assembly.

In one or more embodiments, the ground ring comprises a tubular shape defining an inner diameter of about 2.1 millimeters, an outer diameter of about 3.2 millimeters, and a length of about 3.8 millimeters.

In one or more embodiments, the ground ring comprises a top ground tab configured to contact the electronic board of the biosensor module board and a bottom ground tab configured to contact the RF detection board.

Additionally, an illustrative connector assembly may include a body portion and a coaxial RF connector. The body portion may define a first surface and a second surface opposite the first surface. The coaxial RF connector may be positioned in the body portion and extending between the first surface and the second surface. The coaxial RF connector may include a ground ring, an RF pin positioned within the ground ring, and dielectric therebetween. The connector assembly may be configured to be coupled to an RF detection board such that the coaxial RF connector is operably coupled thereto. The connector assembly may also be configured to be connected to a biosensor module board such that the coaxial RF connector is operably connected thereto.

In one or more embodiments, the coaxial RF connector is configured to conduct frequencies greater than or equal to 2 GHz and dissipate into the ground ring.

In one or more embodiments, the dielectric comprises Teflon.

In one or more embodiments, the RF connector further comprises one or more other connectors positioned in the body portion.

In one or more embodiments, the coaxial RF connector is operably connected to the biosensor module board proximate the first surface of the connector assembly and the coaxial RF connector is operably coupled to the RF detection board proximate the second surface of the connector assembly.

In one or more embodiments, the ground ring comprises a tubular shape defining an inner diameter of about 2.1 millimeters, an outer diameter of about 3.2 millimeters, and a length of about 3.8 millimeters.

In one or more embodiments, the ground ring comprises a top ground tab configured to contact the electronic board of the biosensor module board and a bottom ground tab configured to contact the RF detection board.

Also, an illustrative method may include providing a connector assembly comprising a coaxial RF connector. The coaxial RF connector may include a ground ring, an RF pin positioned within the ground ring, and dielectric therebetween. The connector assembly may be operably coupled to an RF detection board. The method may also include attaching a first biosensor module board to the connector assembly such that the coaxial RF connector is operably connected to the first biosensor module board. The first biosensor module board may include an electronic board and a fluidic sensor device. Further, the method may include removing the first biosensor module board from the connector assembly and attaching a second biosensor module board to the connector assembly such that the coaxial RF connector is operably connected to the second biosensor module board. The second biosensor module board may include an electronic board and a fluidic sensor device.

In one or more embodiments, the coaxial RF connector is configured to conduct frequencies greater than or equal to 2 GHz and dissipate into the ground ring.

In one or more embodiments, attaching a first biosensor module board to the connector assembly comprises directly contacting the ground ring and the electronic board of the first biosensor module board and attaching a second biosensor module board to the connector assembly comprises directly contacting the ground ring and the electronic board of the second biosensor module board.

In one or more embodiments, the ground ring comprises a top ground tab configured to contact the electronic board of the biosensor module board and a bottom ground tab configured to contact the RF detection board.

The above summary is not intended to describe each embodiment or every implementation. Rather, a more complete understanding of illustrative embodiments will become apparent and appreciated by reference to the following Detailed Description of Selected Embodiments and Claims in view of the accompanying figures of the drawing.

BRIEF DESCRIPTION OF DRAWINGS

Exemplary embodiments will be further described with reference to the figures of the drawing, wherein.

Figure 1:
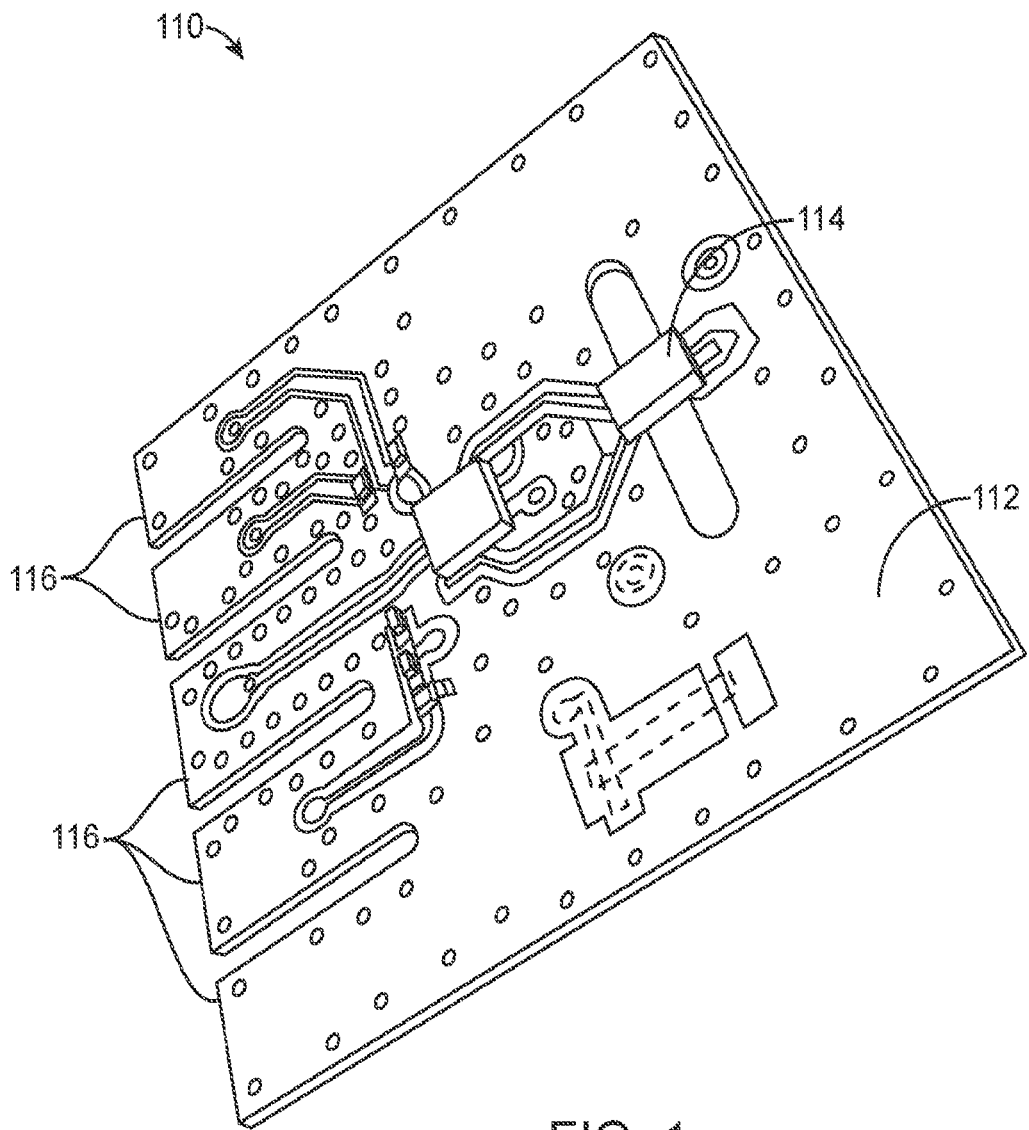
FIG. 1 illustrates a biosensor module board including a bulk acoustic wave (BAW) sensor device.

The figures are rendered primarily for clarity and, as a result, are not necessarily drawn to scale. Moreover, various structure/components may be shown diagrammatically or removed from some or all of the views to better illustrate aspects of the depicted embodiments, or where inclusion of such structure/components is not necessary to an understanding of the various exemplary embodiments described herein. The lack of illustration/description of such structure/components in a particular figure is, however, not to be interpreted as limiting the scope of the various embodiments in any way. Still further, "Figure x" and "FIG. x" may be used interchangeably herein to refer to the figure numbered x.

DETAILED DESCRIPTION

In the following detailed description, several specific embodiments of devices, systems and methods are disclosed. It is to be understood that other embodiments are contemplated and may be made without departing from the scope or spirit of the present disclosure. Reference is made to the accompanying figures of the drawing which form a part hereof. It is to be understood that other embodiments, which may not be described and/or illustrated herein, are certainly contemplated. The following detailed description, therefore, is not to be taken in a limiting sense.

The present disclosure relates to connector assemblies and their use within systems including biosensor module boards and interrogating instruments (e.g., including an RF detection board). The connector assembly may be coupled to the RF detection board such that one or more biosensor module boards may be removably coupled to the RF detection board (e.g., one at a time). In other words, the present disclosure describes a reliable, repeatable blind electrical connection between a biosensor module and an RF detection board with minimal mechanical wear. Further, the connector assembly may include a coaxial RF connector that includes both a ground ring and an RF pin positioned therein for reliable operation over a broad spectrum of frequencies.

With prior connector assemblies, the RF pin and RF ground (e.g., a common ground) may be positioned some distance from one another. As a result, the RF power transmitted through these prior connector assemblies may not flow to the intended ground and, instead, may radiate to less desirable portions of the biosensor module board. The undesirable radiation of RF power flow may be more noticeable and/or significant at higher frequencies. Further, the bulk acoustic wave (BAW) sensor device (e.g., a fluidic sensor device) located on the biosensor module board may benefit from increased sensitivity of higher frequencies. However, because the higher frequencies may also result in radiative ground RF power, any benefit to the BAW sensor may be reduced (e.g., due to the unreliable RF power flow).

When operating the system at a higher radio frequency (e.g., greater than 2000 MHz), the arrangement as described in the present disclosure, for example, including the source and the ground in close proximity (e.g., a coaxial arrangement), assists the RF signal in following the same path from and back to the coaxial RF connector as described herein. Specifically, when the system is modified to operate at about 2900 MHz, the flow of the RF path may not affect the BAW sensor device in undesirable ways. Therefore, the BAW sensor device may operate in more predictable and reliable ways.

In the following detailed description several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

FIG. 1 illustrates a biosensor module board 110 including an electronic board 112 and a fluidic sensor device 114 (e.g., a bulk acoustic wave (BAW) sensor device). The fluidic sensor device 114 may define at least one surface area region on which a functionalization material is disposed. The at least one surface area region including the functionalization material may be described as a bio-active area upon which a sample material may bind with the functionalization material. It is noted that, in some embodiments, the at least one surface area region may not include a functionalization material (e.g., if the surface area region is configured to act as a control.)

Further, the fluidic sensor device 114 may be mechanically and electrically coupled to the electronic board 112 through contacts/posts. Specifically, the fluidic sensor device 114 may be operably coupled to the electronic board 112 such that a frequency signal may be transmitted between the fluidic sensor device 114 and the electronic board 112. The biosensor module board 110 with the fluidic sensor device 114 may be configured to receive a sample material and measure differing frequency shifts based on the degree to which the sample material binds with the functionalization material.

Figure 2:
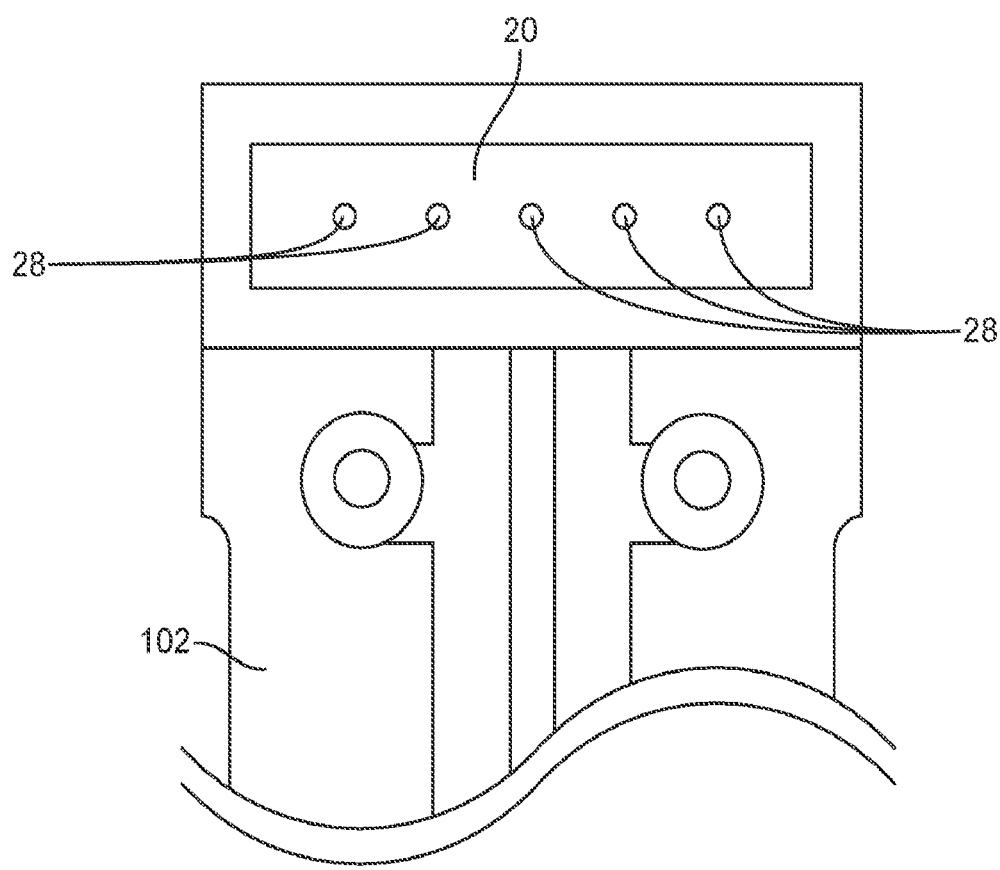
FIG. 2 illustrates a prior art connector attached to the interrogating instrument (e.g., including a radio frequency (RF) detection board).

The electronic board 112 may also include one or more contacts through which the biosensor module board 110 is operably coupled to an RF detection board 102 (e.g., shown in FIG. 2). For example, as shown in FIG. 1, the biosensor module board 110 may include five protrusions 116 having a contact located thereon (e.g., on the side that is not shown in FIG. 1) that is associated with a different type of coupling. Specifically, the five contacts located on the protrusions may be associated with DC power, ground, RF pathway, digital control line, and a conductivity meter electrode (Hematocrit).

A prior art connector 20 attached to an interrogating instrument (e.g., including an RF detection board 102) is illustrated in FIG. 2. The connector 20 includes five terminals 28 and is contained within a molded plastic body. For example, the connector 20 is a surface mount device that contains locating pins in the plastic over-mold that assists in positioning the connector 20 on the biosensor module board 110 such that the terminals align with signal traces on the electronic board 112 of the biosensor module board 110 (e.g., at the protrusions 116). Specifically, the five terminals of the connector 20 correspond to the five contact points of the biosensor module board 110.

Historically these prior connectors have operated effectively at an operating frequency of 2000 MHz or lower. Further, it was shown that operating the system at higher frequencies (e.g., about 2900 MHz) may produce higher mass sensitivity and, therefore more precise results. However, operating at a higher frequency (e.g., about 2900 MHz) uncovered a number of issues with the prior connector that were undetected at lower frequencies. For example, the RF performance of the system was poor at these higher frequencies because the RF flow path to ground produced by the prior connector was unclear and inconsistent.

Figure 3A:
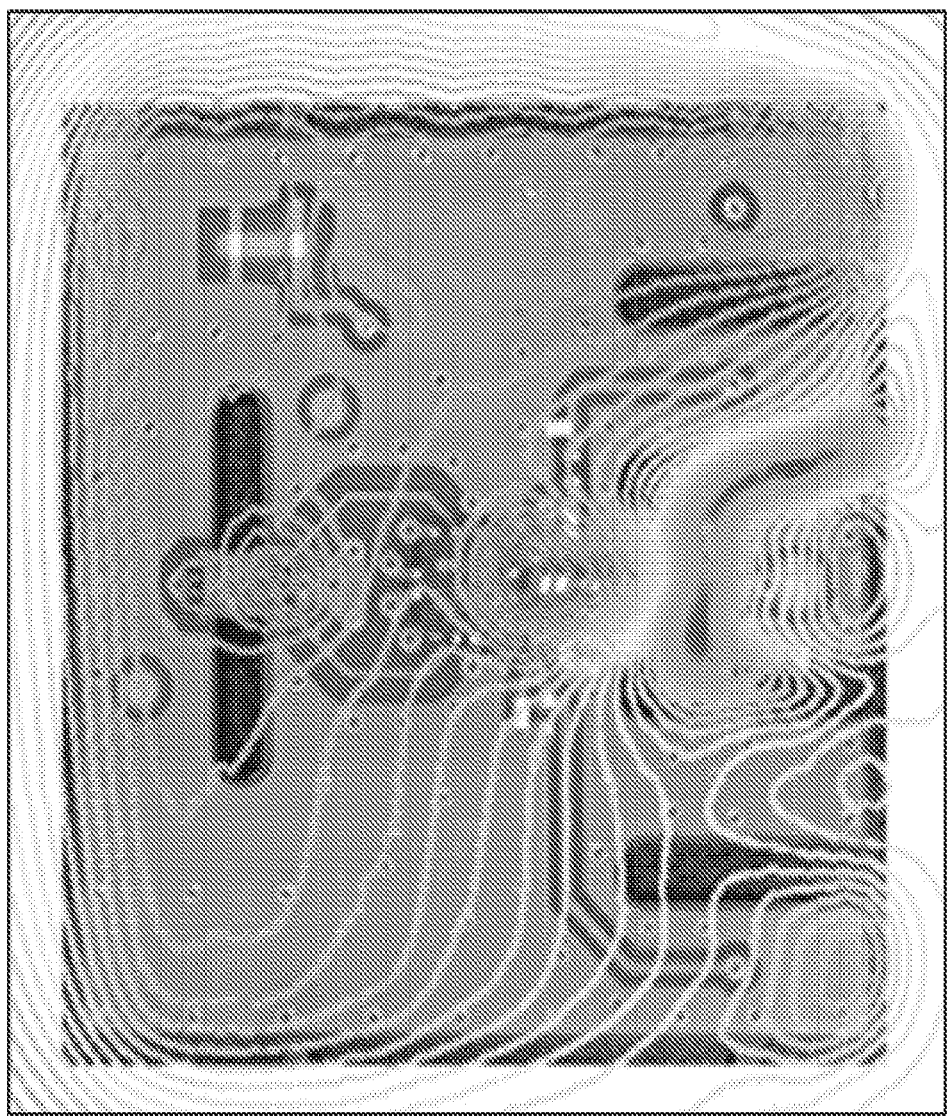
FIG. 3A illustrates an E-Field contour plot of the biosensor module board of FIG. 1 using the prior art connector of FIG. 2.
Figure 3B:
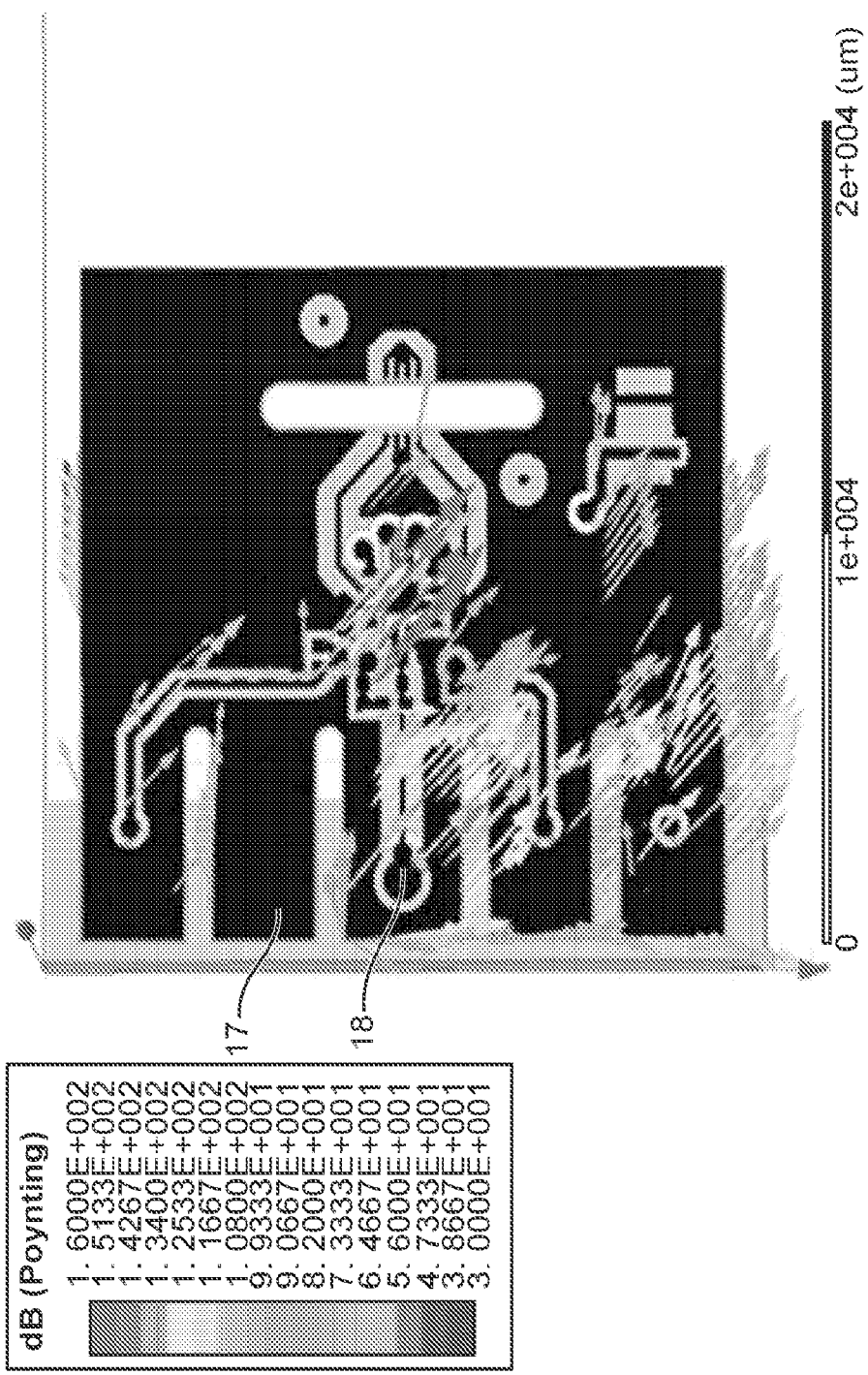
FIG. 3B illustrates a Poynting Vector analysis of the biosensor module board of FIG. 1 using the prior art connector of FIG. 2.

As shown in FIGS. 3A and 3B, the RF power flow may not be through the intended ground (e.g., located at a contact point directly adjacent to the RF source) when using the prior connector at higher frequencies (e.g., about 2900 MHz). For example, FIG. 3A shows an E-field contour plot that represents the RF power flow through the biosensor module board (e.g., when the RF source is connected to the middle contact protrusion) when using the prior connector. The red shown in the plot indicates high fields and the purple in the plot indicates low fields. Overall, the E-field contour plot indicates that the biosensor module board is acting as a radiating antenna with high radiation fields at the top and right edges of the board (e.g., as oriented in FIG. 3A). This suggests that the return path for the RF power flow may not be through the intended ground. Instead, the RF power flow is radiating into the surrounding space because it is a lower impedance path. As a result, external sources or environment could potentially change characteristics of the system due to the radiative nature of the RF power flow associated with the prior connector.

As a result of the radiating RF power flow, the system is prone to instability because the smallest changes in positioning of the biosensor module board may change the RF characteristics of the system and ultimately of the sensor measurements that are being made. For example, the RF measurements are used to determine what is being sensed by the fluidic sensor device and, therefore, any disruption may alter or disrupt what is being sensed. Further testing showed that the intended ground path positioned on the prior connector can be removed with no change in the resulting RF filed pattern, which confirms that the RF ground is a radiative ground when using the prior connector. Similarly, FIG. 3B illustrates a Poynting Vector analysis of the magnitude and direction of RF power flow through the biosensor module board, showing that the RF power is flowing down and to the right (e.g., indicating a radiative ground when using the prior connector) as shown in the orientation of FIG. 3B. Further, for example, the intended ground is connected to protrusion 17 (e.g., as shown in FIG. 3B) and the RF source is connected to protrusion 18 (e.g., the center protrusion). As shown in FIG. 3B, the RF power flow radiates away from the intended ground connection 17 indicating that the intended ground connection 17 is not acting as a ground for the RF power flow.

The root cause of the radiative ground in the biosensor module board may be caused by the separation of the RF input and ground return paths. The existing structure of the prior connector may not be capable of providing a proper pathway for RF power flow via displacement current in the dielectric material because of the physical distance between the source and the ground (e.g., the RF source located at the central contact point of the biosensor module board and the intended ground located at a contact point directly adjacent thereto). In order to solve this problem, the prior connector would need to be replaced in such a way that would allow propagation of the forward and reflected RF power within the provided space configuration.

Figure 4:
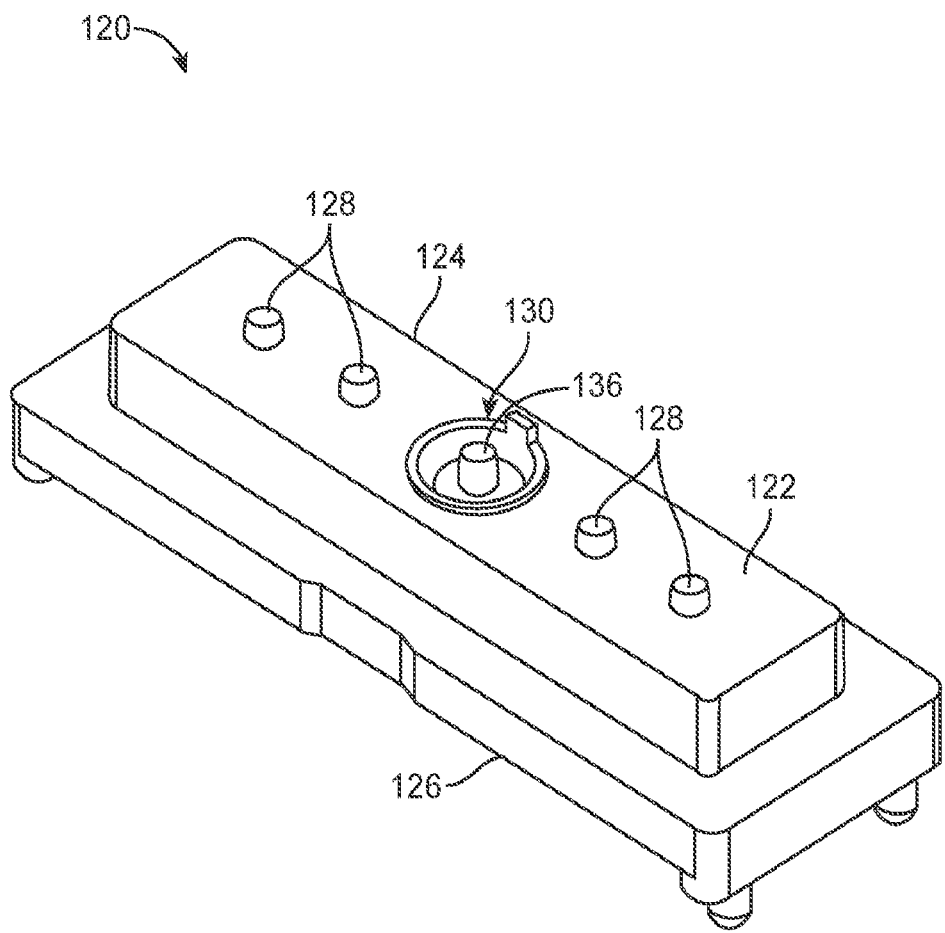
FIG. 4 illustrates a top perspective view of an exemplary connector assembly according to the present disclosure.
Figure 5A:
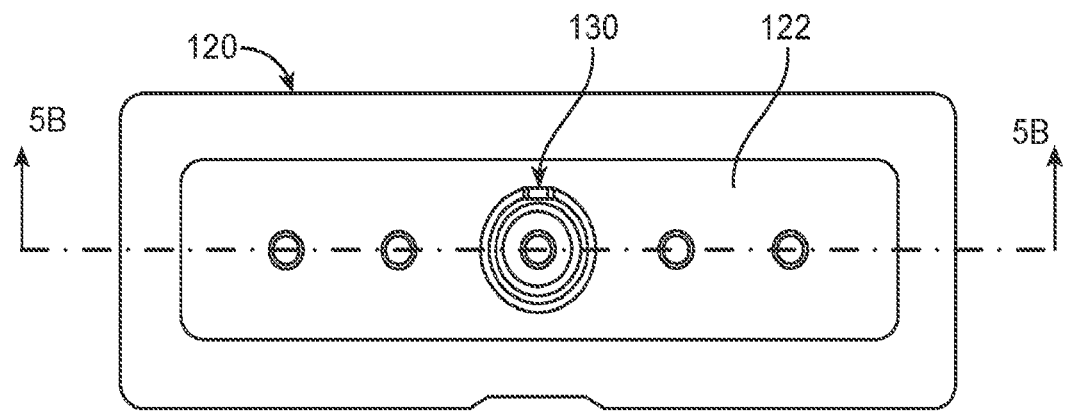
FIG. 5A illustrates a top plan view of the connector assembly of FIG. 4.
Figure 5B:
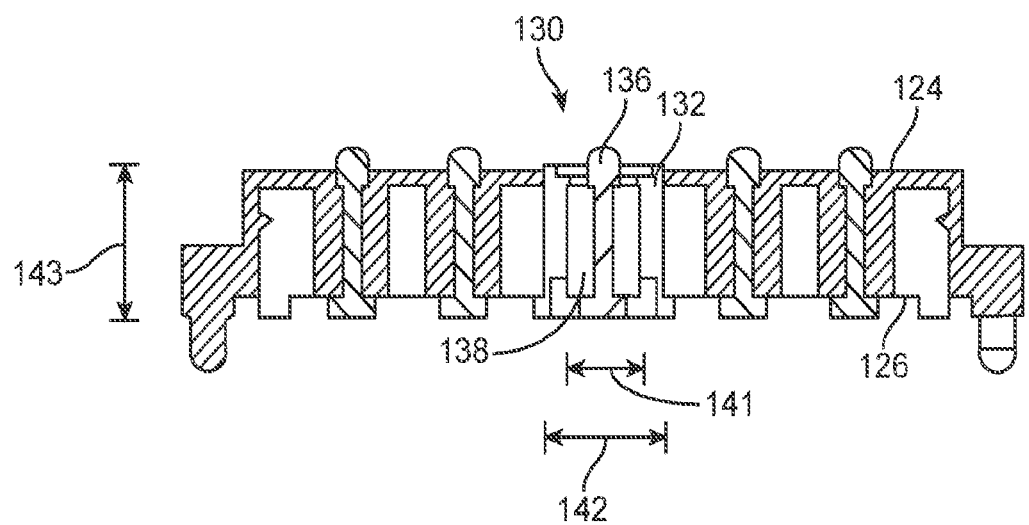
FIG. 5B illustrates a cross-section of the connector assembly of FIG. 5A taken across line 5B-5B of FIG. 5A.

FIGS. 4, 5A, and 5B illustrate an exemplary connector assembly in accordance with the present disclosure. The connector assembly 120 may be operably coupled to the RF detection board 102 (e.g., as shown in FIG. 2) and may be configured to be operably connected to the biosensor module board 110. For example, the connector assembly 120 may be fixedly coupled to the RF detection board 102 and removably coupled to the biosensor module board 110 such that any number of biosensor module boards may be coupled to and removed from the RF detection board 102 (e.g., via the connector assembly 120). Specifically, the RF detection board 102 may be part of the interrogating instrument upon which multiple biosensor module boards (e.g., including sample material thereon) are positioned to test the sample material on the biosensor module board. Further, the biosensor module board 110 and connector assembly 120 may be configured such that they are removably couplable through a non-sliding compression contact (e.g., a coaxial arrangement). Although any connection configuration is herein contemplated.

The connector assembly 120 may include a coaxial RF connector 130. The coaxial RF connector 130 may include a ground ring 132, an RF pin 136 positioned within the ground ring 132, and a dielectric 138 therebetween. The RF pin 136 may provide a conduit through which an RF signal may be transmitted to the biosensor module board 110 (e.g., the fluidic sensor device 114) and the ground ring 132 may provide an RF ground source for the RF flow to return (e.g., the RF return path may be along the inner surface of the ground ring 132).

Specifically, the coaxial RF connector 130 may be arranged and/or configured such that a proper pathway is provided for RF power flow from the RF pin 136 and to the ground ring 132 at higher frequencies. For example, the source and ground are configured to support RF wave propagation in the dielectric 138 and, therefore, provide a proper pathway. Specifically, the coaxial RF connector 130 may be configured to conduct frequencies greater than or equal to 2 GHz, greater than or equal to 2.25 GHz, greater than or equal to 2.5 GHz, greater than or equal to 2.75 GHz, greater than or equal to 2.9 GHz, etc. and for the RF flow to dissipate into the ground ring 132 (e.g., without radiating and creating issues like the prior connector).

The RF pin 136 may be positioned at the center of the ground ring 132 with the dielectric 138 extending completely therebetween (e.g., to electrically isolate the ground ring 132 from the RF pin 136). The dielectric 138 may include any suitable material that insulates between the RF pin 136 and the ground ring 132. For example, the dielectric may include Teflon, Vectra, polyethylene, various ceramics, etc. The ground ring 132 and the RF pin 136 may include any suitable material to conduct RF flow. For example, one or both of the ground ring 132 and the RF pin 136 may include brass or copper alloys (e.g., typically plated in gold or silver alloys suitable for electrical contacts). Specifically, the combination of the brass tube ground ring 132 and the Teflon dielectric 138 may result in a section of coaxial line with characteristic impedance of about 50 Ohms.

The coaxial RF connector 130 may extend through the connector assembly 120 (e.g., a body portion 122 of the connector assembly 120) between a first surface 124 (e.g., a top surface) and a second surface 126 (e.g., a bottom surface) opposite the first surface 124. The coaxial RF connector 130 may be operably connected to the biosensor module board 110 proximate the first surface 124 of the connector assembly 120 and the coaxial RF connector 130 may be operably coupled to the RF detection board 102 proximate the second surface 126 of the connector assembly 120. In other words, one or both of the ground ring 132 and the RF pin 136 may extend a distance at least through the body portion 122 of the connector assembly 120 between the first and second surfaces 124, 126.

Figure 6A:
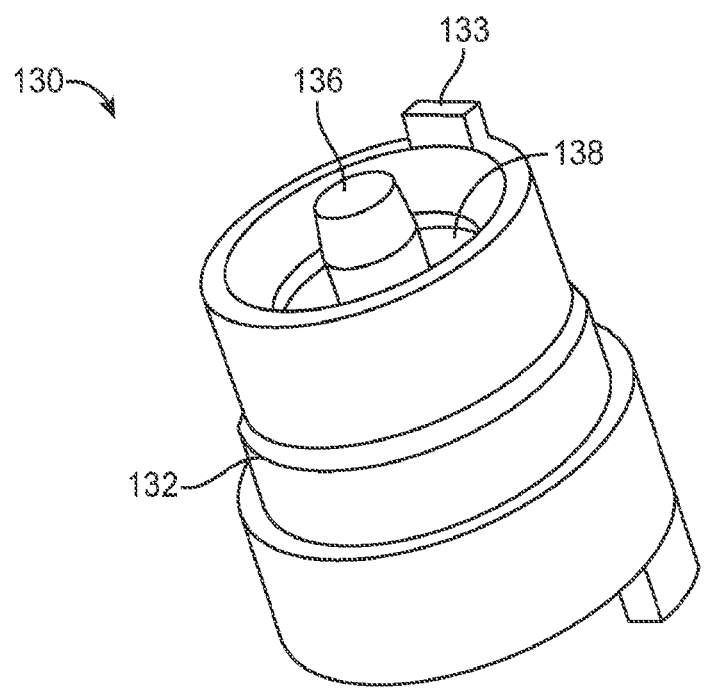
FIG. 6A illustrates a top perspective view of an exemplary coaxial RF connector of the connector assembly of FIG. 4A, isolated from the connector assembly.
Figure 6B:
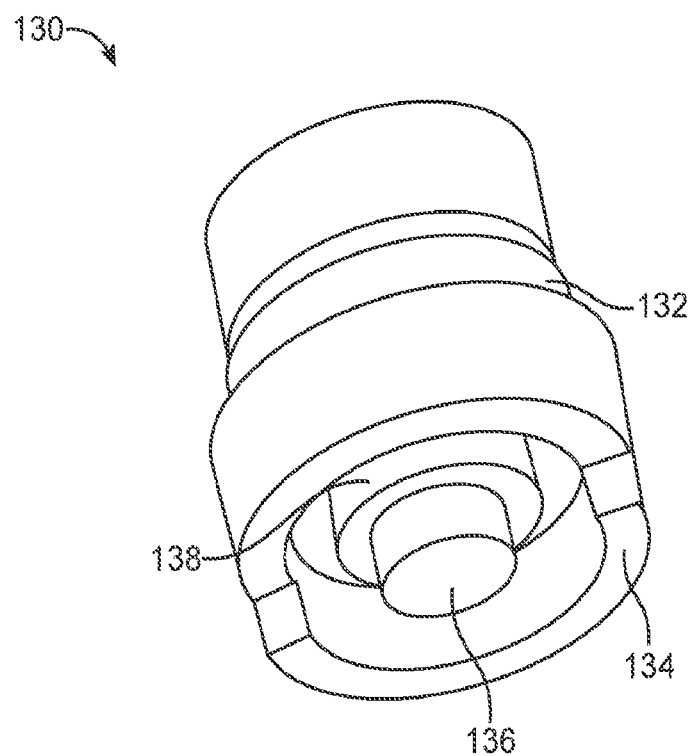
FIG. 6B illustrates a bottom perspective view of the coaxial RF connector of FIG. 6A.

The ground ring 132, as shown in FIGS. 6A and 6B, of the coaxial RF connector 130 may include any suitable shape and dimensions. It is noted that the dimensions may be determined based on the dielectric material used and the characteristic impedance desired for the system/application. For example, the ground ring 132 (as shown in FIG. 5B) of the coaxial RF connector 130 may include a tubular shape defining an inner diameter 141 of greater than or equal to 1.5 millimeters, greater than or equal to 2 millimeters, etc. and/or less than or equal to 2.5 millimeters, less than or equal to 2.1 millimeters, etc., an outer diameter 142 of greater than or equal to 2.5 millimeters, greater than or equal to 3 millimeters, etc. and/or less than or equal to 4 millimeters, less than or equal to 3.5 millimeters, less than or equal to 3.2 millimeters, etc., and a length 143 of greater than or equal to 2.5 millimeters, greater than or equal to 3 millimeters, greater than or equal to 3.5 millimeters, etc. and/or less than or equal to 5 millimeters, less than or equal to 4.5 millimeters, less than or equal to 4 millimeters, less than or equal to 3.8 millimeters, etc. In other words, the ground ring 132 of the coaxial RF connector 130 may include a tubular shape defining an inner diameter 141 of about 1.5 to 2.5 millimeters, an outer diameter 142 of about 2.5 to 4 millimeters, and a length of about 2.5 to 5 millimeters.

Specifically, the ground ring 132 of the coaxial RF connector 130 may include a tubular shape defining an inner diameter 141 of about 2.1 millimeters, an outer diameter 142 of about 3.2 millimeters, and a length 143 of about 3.8 millimeters. Further, the ground ring 132 may include a top ground tab 133 configured to operably contact the biosensor module board 110 to provide a ground source for RF flow from the biosensor module board 110. In one or more embodiments, the ground ring 132 may directly contact the electronic board 112 of the biosensor module board 110. In other words, the electronic board 112 of the biosensor module board 110 may not include an additional connector to interface with the connector assembly 120. The position of the top ground tab 133 of the ground ring 130 may be located such that the path length distance between the conductive paths in the RF circuit are minimized (e.g., nearest the fluidic sensor device 114 of the biosensor module board 110)

The ground ring 132 may also include a bottom ground tab 134 configured to operably contact the RF detection board 102 to continue the ground path to the RF detection board 102. Furthermore, in one or more embodiments, a copper ribbon may be attached between the ground plane of the RF detection board 102 and the ground ring 132.

The connector assembly 120 may also include one or more other connectors 128 or terminals (e.g., to maintain a similar form factor and structure as prior connector 20 shown in FIG. 2). For example, as shown in FIG. 4, the coaxial RF connector 130 is positioned in the middle while two other connectors 128 are located on either side of the coaxial RF connector 130. The connector assembly 120 may include any suitable other connectors 128. For example, as described herein, the other connectors may be associated with the protrusions of the biosensor module board 110 and correspond to DC power, a digital control line, a conductivity meter electrode, and a ground pin (e.g., to ground the other connectors 128). As such the connector assembly 120 may integrate digital analog and high frequency RF flow without perturbing the RF signal. For example, in the prior connector, one of the adjacent connectors/pins to the RF signal pin was a ground connection. The physical separation of the RF signal pin and the ground of the prior connector did not provide for proper wave-guiding of the RF signal (which, e.g., led to radiated emissions and poor performance).

Figure 7:
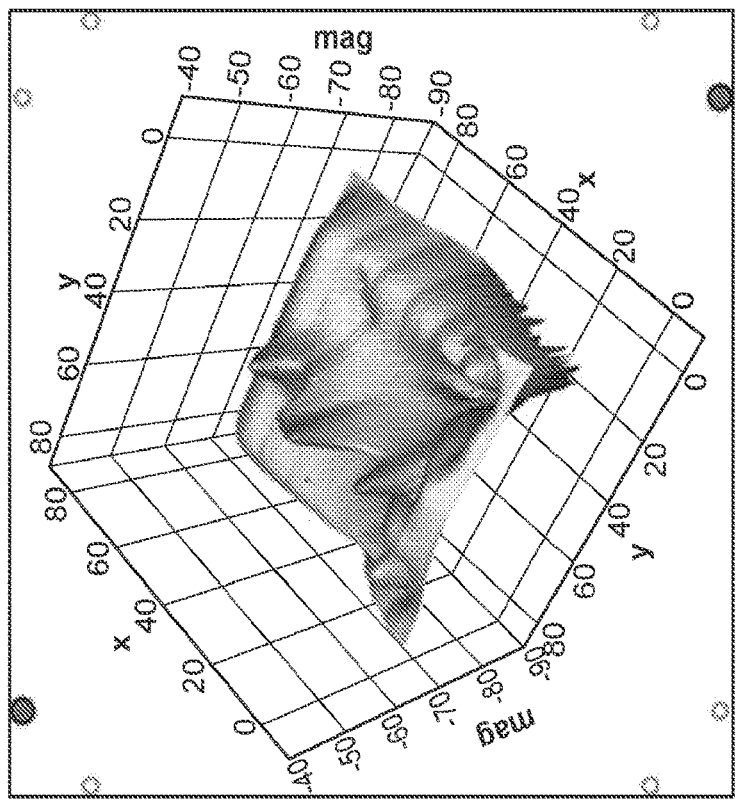
FIG. 7 illustrates an E-Field contour and surface plots of the biosensor module board of FIG. 1 using the exemplary connector assembly of FIG. 4A.
Figure 7:
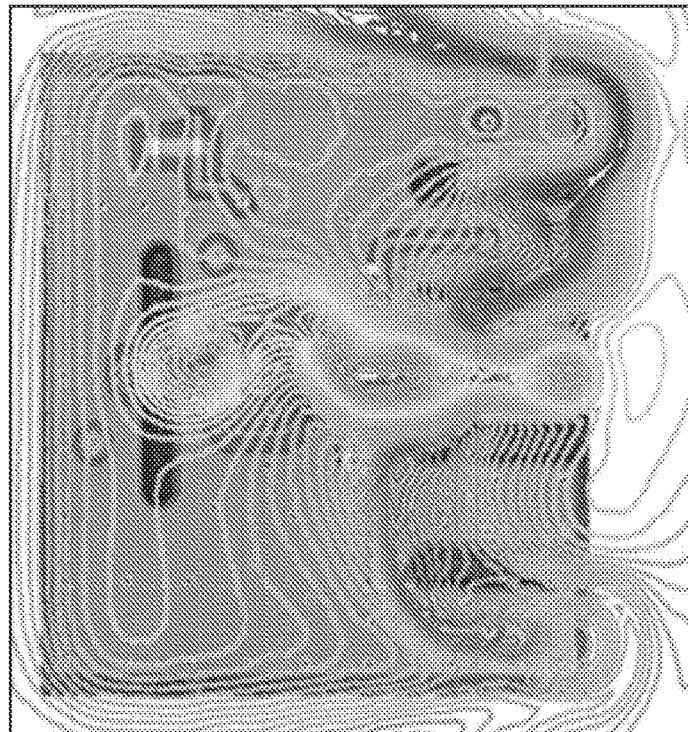
Figure 7:
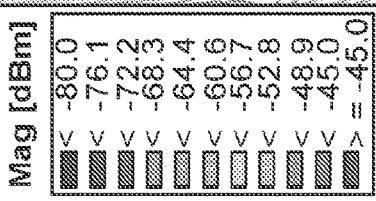

An E-field contour and surface plots of the of the biosensor module board 110 using the connector assembly 120 is shown in FIG. 7. As shown, the RF power flow extends from the center protrusion 116 of the biosensor module board 110 with the reflected RF power following the same path back to the center protrusion (e.g., the location of the coaxial RF connector 130). Radiative power flow to the sides of the biosensor module board 110 are greatly reduced as compared to the prior connector (e.g., as shown in FIG. 3A).

Figure 8:
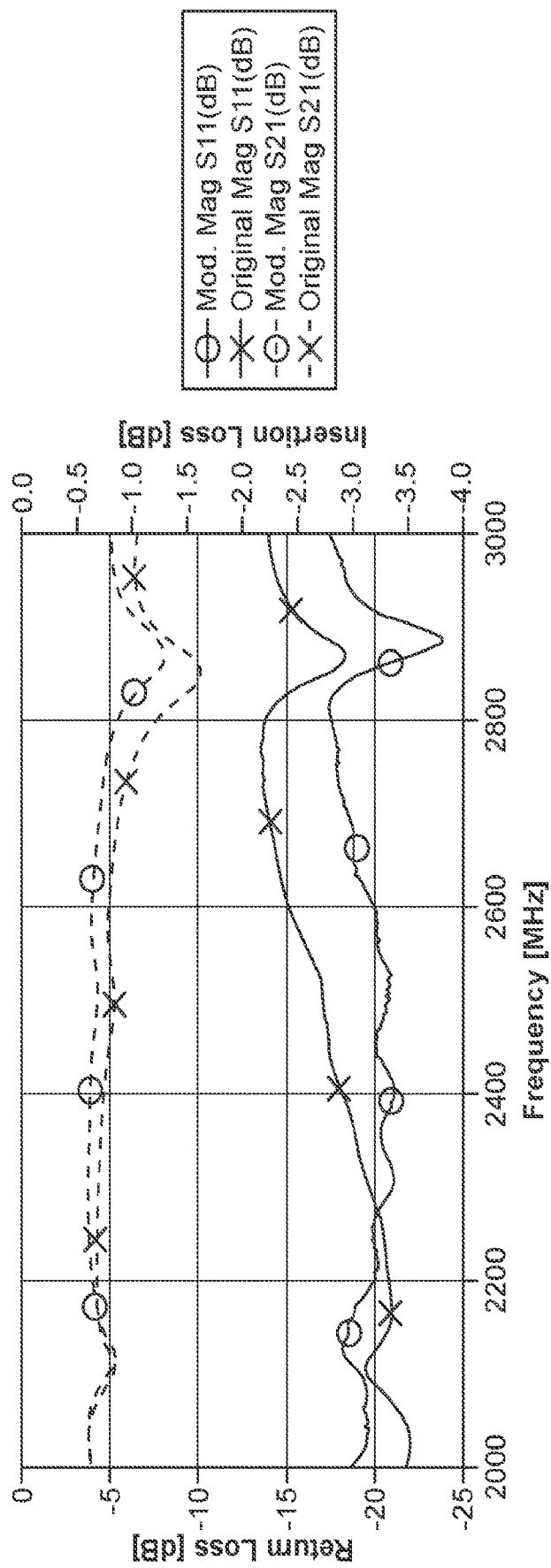
FIG. 8 illustrates S-parameter data comparing the prior art connector of FIG. 2 with the exemplary connector assembly of FIG. 4A.

Further, a comparison of the S-parameter data for the prior (original) connector versus the present connector assembly 120 is shown in FIG. 8. The chart of FIG. 8 shows the improvement in return loss and insertion loss of the connection when comparing the present connector assembly 120 to the prior connector. For example, present connector assembly 120 is represented with circles (e.g., red lines) and identified as "Mod. Mag" while the prior connector is represented with diagonals (e.g., black lines) and identified as "Original Mag." Additionally, the insertion loss data is represented with dashed lines and the return loss data is represented with solid lines. As shown in FIG. 8, the present connector assembly 120 has an insertion loss closer to zero than the prior connector and a return loss that is lower than the prior connector.

Figure 9:
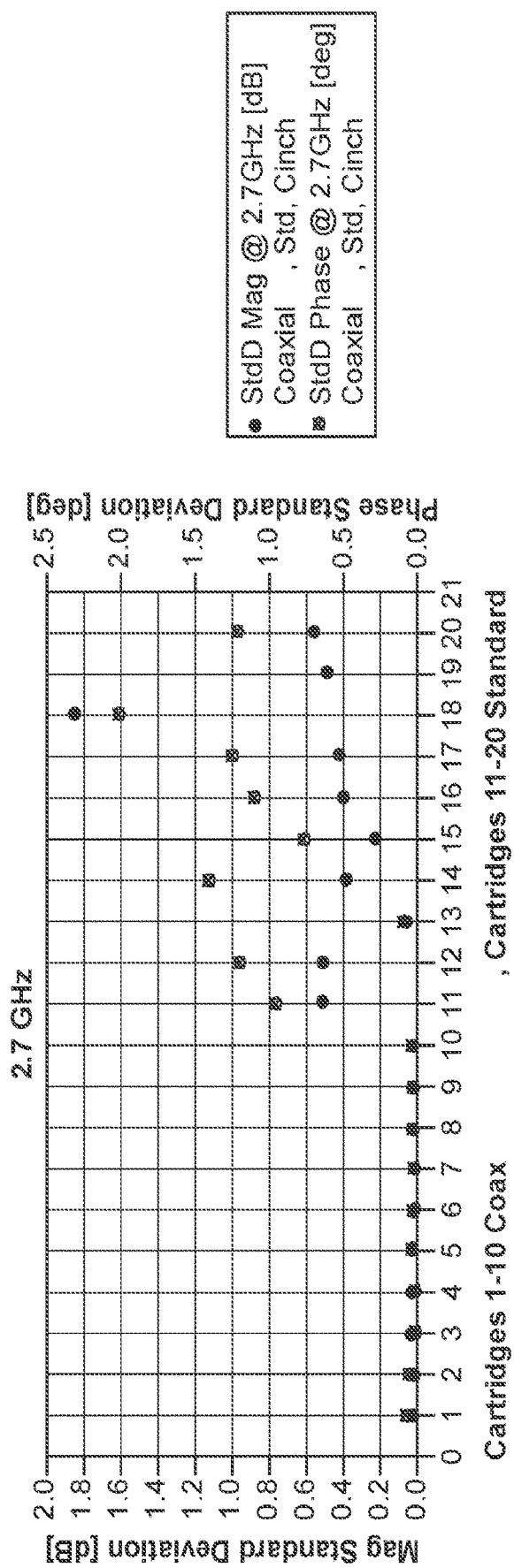
FIG. 9 illustrates Reliability and Repeatability results of testing and comparing the prior art connector of FIG. 2 with the exemplary connector assembly of FIG. 4A.

Additionally, a connection reliability and repeatability study was performed on the prior connector (e.g., as shown in FIG. 2) and the present connector assembly 120 for comparison and proof of performance gains. Test cartridges were prepared for each connector. Each cartridge was inserted and measured by the instrument 100 times across ten cartridges. The variation in the S-parameter magnitude and phase was monitored. Standard deviation at 2.7 GHz was computed for each cartridge's 100 data sets and plotted. Cartridges 1 through 10 were tested with the present connector assembly 120 installed, Cartridges 11 through 20 were tested with the prior connector installed. A significant performance in connector repeatability can be seen by the present connector assembly 120 as compared to the prior connector, e.g., as shown in FIG. 9 (e.g., values from connector assembly 120 are approximately zero). Furthermore, there were no connection failures for any of the connector assembly 120 tests.

Figure 10:
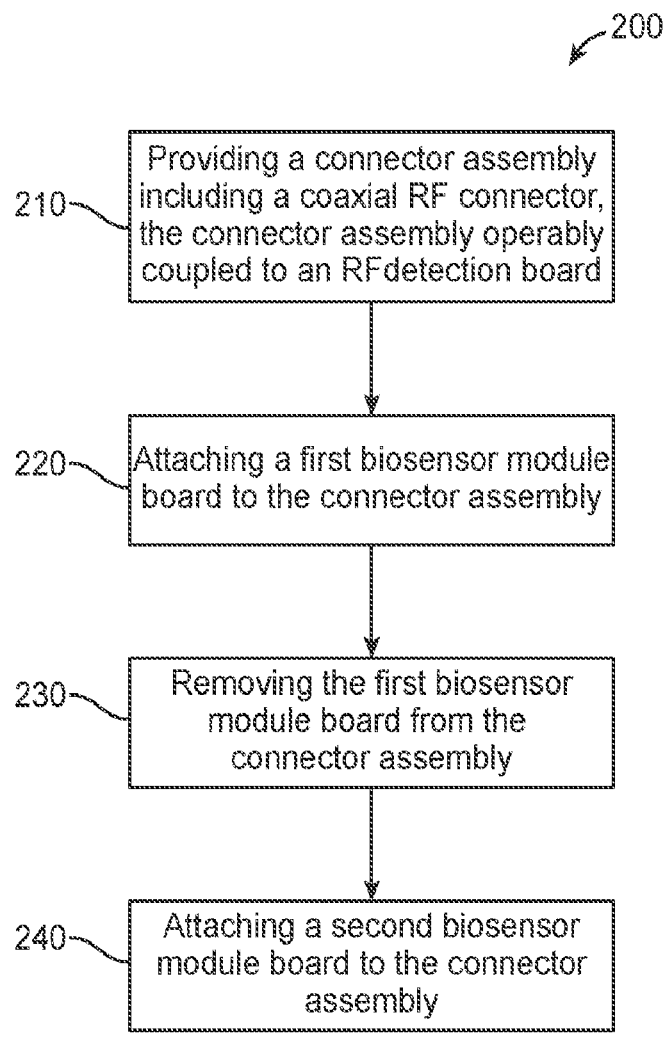
FIG. 10 illustrates a method of attaching a first biosensor module board to a connector assembly, removing the first biosensor module board from the connector assembly, and attaching a second biosensor module board to the connector assembly.

An illustrative method 200 of attaching and removing a first biosensor module board to a connector assembly and attaching a second biosensor module board to the connector assembly is illustrated in FIG. 10. The method 200 may include providing 210 a connector assembly including a coaxial RF connector. The coaxial RF connector may include a ground ring, an RF pin positioned within the ground ring, and dielectric therebetween. Further, the connector assembly may be operably coupled to an RF detection board. The method may also include attaching 220 a first biosensor module board to the connector assembly such that the coaxial RF connector may be operably connected to the first biosensor module board. The first biosensor module board may include an electronic board and a fluidic sensor device. The method may further include removing 230 the first biosensor module board from the connector assembly and attaching 240 a second biosensor module board to the connector assembly such that the coaxial RF connector may be operably connected to the second biosensor module board. The second biosensor module board may also include an electronic board and a fluidic sensor device (e.g., similar to the first biosensor module board, but potentially containing a different sample material contained therein). The repeatable connection of multiple biosensor module boards using the present connector assembly removed the radiative nature of the ground path, making a proper RF transmission line and allowing for a very repeatable RF transmission line characteristics.

It is noted that the connection made by the coaxial RF connector is between two boards and does not include cable therebetween. In other words, the coaxial RF connector is in direct contact with both the RF detection board and the electronic board of the biosensor module board.

In one or more embodiments, the coaxial RF connector may be configured to conduct frequencies greater than or equal to 2 GHz and dissipate into the ground ring. In one or more embodiments, attaching 220 a first biosensor module board to the connector assembly may include directly contacting the ground ring and the electronic board of the first biosensor module board and attaching a second biosensor module board to the connector assembly may include directly contacting the ground ring and the electronic board of the second biosensor module board. In one or more embodiments, the ground ring may include a top ground tab configured to contact the electronic board of the biosensor module board and a bottom ground tab configured to contact the RF detection board Illustrative embodiments are described and reference has been made to possible variations of the same. These and other variations, combinations, and modifications will be apparent to those skilled in the art, and it should be understood that the claims are not limited to the illustrative embodiments set forth herein.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to." It will be understood that "consisting essentially of," "consisting of," and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

What is claimed is:

1. A system comprising:
   an RF detection board;
   a biosensor module board comprising an electronic board and a fluidic sensor device; and
   a connector assembly operably coupled to the RF detection board and configured to be operably connected to the biosensor module board, wherein the connector assembly comprises a coaxial RF connector, wherein the coaxial RF connector comprises a ground ring, an RF pin positioned within the ground ring, and a dielectric therebetween.

2. The system of claim 1, wherein the coaxial RF connector is configured to conduct frequencies greater than or equal to 2 GHz and dissipate into the ground ring.

3. The system of claim 1, wherein the coaxial RF connector is configured to conduct frequencies greater than or equal to 2.5 GHz and dissipate into the ground ring.

4. The system of claim 1, wherein the dielectric comprises Teflon.

5. The system of claim 1, wherein an RF signal is configured to be transmitted from the RF pin to the fluidic sensor device and then to the ground ring.

6. The system of claim 1, wherein the ground ring directly contacts the electronic board of the biosensor module board.

7. The system of claim 1, wherein the coaxial RF connector extends through the connector assembly between a first surface and a second surface, wherein the coaxial RF connector is operably connected to the biosensor module board proximate the first surface of the connector assembly and the coaxial RF connector is operably coupled to the RF detection board proximate the second surface of the connector assembly.

8. The system of claim 1, wherein the ground ring comprises a tubular shape defining an inner diameter of about 2.1 millimeters, an outer diameter of about 3.2 millimeters, and a length of about 3.8 millimeters.

9. The system of claim 1, wherein the ground ring comprises a top ground tab configured to contact the electronic board of the biosensor module board and a bottom ground tab configured to contact the RF detection board.

10. A connector assembly comprising:
    a body portion defining a first surface and a second surface opposite the first surface; and
    a coaxial RF connector positioned in the body portion and extending between the first surface and the second surface, wherein the coaxial RF connector comprises a ground ring, an RF pin positioned within the ground ring, and a dielectric therebetween,
    wherein the connector assembly is configured to be coupled to an RF detection board such that the coaxial RF connector is operably coupled thereto, and wherein the connector assembly is configured to be connected to a biosensor module board such that the coaxial RF connector is operably connected thereto.

11. The connector assembly of claim 10, wherein the coaxial RF connector is configured to conduct frequencies greater than or equal to 2 GHz and dissipate into the ground ring.

12. The connector assembly of claim 10, wherein the dielectric comprises Teflon.

13. The connector assembly of claim 10, wherein the coaxial RF connector further comprises one or more other connectors positioned in the body portion.

14. The connector assembly of claim 10, wherein the coaxial RF connector is operably connected to the biosensor module board proximate the first surface of the connector assembly and the coaxial RF connector is operably coupled to the RF detection board proximate the second surface of the connector assembly.

15. The connector assembly of claim 10, wherein the ground ring comprises a tube defining an inner diameter of about 2.1 millimeters, an outer diameter of about 3.2 millimeters, and a length of about 3.8 millimeters.

16. The connector assembly of claim 10, wherein the ground ring comprises a top ground tab configured to contact an electronic board of the biosensor module board and a bottom ground tab configured to contact the RF detection board.

17. A method comprising:
provide a connector assembly comprising a coaxial RF connector, wherein the coaxial RF connector comprises a ground ring, an RF pin positioned within the ground ring, and a dielectric therebetween, wherein the connector assembly is operably coupled to an RF detection board;
attaching a first biosensor module board to the connector assembly such that the coaxial RF connector is operably connected to the first biosensor module board, wherein the first biosensor module board comprises an electronic board and a fluidic sensor device;
removing the first biosensor module board from the connector assembly; and
attaching a second biosensor module board to the connector assembly such that the coaxial RF connector is operably connected to the second biosensor module board, wherein the second biosensor module board comprises an electronic board and a fluidic sensor device.

18. The method of claim 17, wherein the coaxial RF connector is configured to conduct frequencies greater than or equal to 2 GHz and dissipate into the ground ring.

19. The method of claim 17, wherein attaching the first biosensor module board to the connector assembly comprises directly contacting the ground ring and the electronic board of the first biosensor module board and wherein attaching the second biosensor module board to the connector assembly comprises directly contacting the ground ring and the electronic board of the second biosensor module board.

20. The method of claim 17, wherein the ground ring comprises a top ground tab configured to contact the electronic board of the biosensor module board and a bottom ground tab configured to contact the RF detection board.

* * * * *